US008911351B2

(12) United States Patent
Koide

(10) Patent No.: US 8,911,351 B2
(45) Date of Patent: Dec. 16, 2014

(54) ANTENNA CONNECTION UNIT, RECEIVED STRENGTH CORRECTION APPARATUS AND CAPSULE ENDOSCOPE SYSTEM

(71) Applicant: Olympus Medical Systems Corp., Tokyo (JP)

(72) Inventor: Naoto Koide, Hachioji (JP)

(73) Assignee: Olympus Medical Systems Corp., Tokyo (JP)

( * ) Notice: Subject to any disclaimer, the term of this patent is extended or adjusted under 35 U.S.C. 154(b) by 0 days.

(21) Appl. No.: 14/089,123

(22) Filed: Nov. 25, 2013

(65) Prior Publication Data

US 2014/0163316 A1 Jun. 12, 2014

Related U.S. Application Data

(63) Continuation of application No. PCT/JP2012/076834, filed on Oct. 17, 2012.

(30) Foreign Application Priority Data

Oct. 21, 2011 (JP) ................................. 2011-232185

(51) Int. Cl.
*A61B 1/00* (2006.01)
*A61B 1/04* (2006.01)
*A61B 5/07* (2006.01)

(52) U.S. Cl.
CPC ......... *A61B 1/00016* (2013.01); *A61B 1/00057* (2013.01); *A61B 1/041* (2013.01); *A61B 1/0002* (2013.01); *A61B 1/00045* (2013.01); *A61B 5/073* (2013.01)
USPC ............................ 600/101; 600/118; 600/103

(58) Field of Classification Search
CPC ............... A61B 1/00016; A61B 1/041; A61B 1/00045; A61B 1/0002; A61B 1/00057
USPC .......................................... 600/103, 101, 118
See application file for complete search history.

(56) References Cited

U.S. PATENT DOCUMENTS 7,618,366 B2 * 11/2009 Glukhovsky et al. .......... 600/101
8,632,457 B2 * 1/2014 Nagase et al. ................ 600/103
(Continued)

FOREIGN PATENT DOCUMENTS

JP 2003-608 A 1/2003
JP 2003-19111 A 1/2003
(Continued)

OTHER PUBLICATIONS

International Search Report dated Jan. 15, 2013 from related International Application No. PCT/JP2012/076834.

*Primary Examiner* — John P Leubecker
(74) *Attorney, Agent, or Firm* — Scully, Scott, Murphy & Presser, P.C.

(57) ABSTRACT

An antenna connection unit is a unit to which receiving antennas for receiving a wireless signal transmitted from a capsule endoscope introduced into a subject, is connectable. The antenna connection unit includes a received electric field strength detector configured to detect received strength of the wireless signal according to a plurality of pieces of input power from the receiving antennas, a correction parameter generation unit configured to generate a received strength correction parameter for correcting the received electric field strength detector, which is obtained by correcting the plurality of pieces of input power and the received strength corresponding to each input power, based on a reference parameter indicating a relationship between each input power and a detection strength obtained by performing a measurement for a received electric field strength detection circuit as a reference in advance, and a storage unit for storing the received strength correction parameter.

11 Claims, 10 Drawing Sheets

(56) References Cited

U.S. PATENT DOCUMENTS

| | | |
|---|---|---|
| 2002/0173718 A1 | 11/2002 | Frisch et al. |
| 2003/0085994 A1* | 5/2003 | Fujita et al. .................... 348/77 |
| 2005/0148816 A1 | 7/2005 | Glukhovsky et al. |
| 2008/0108872 A1 | 5/2008 | Glukhovsky et al. |
| 2009/0163772 A1* | 6/2009 | Koide et al. ................... 600/118 |
| 2009/0192348 A1 | 7/2009 | Nishino |
| 2009/0312601 A1* | 12/2009 | Shigemori ................... 600/103 |
| 2010/0022833 A1* | 1/2010 | Nagase ........................ 600/118 |
| 2013/0123575 A1* | 5/2013 | Homan ........................ 600/103 |
| 2013/0158344 A1* | 6/2013 | Taniguchi .................... 600/103 |

FOREIGN PATENT DOCUMENTS

| | | |
|---|---|---|
| JP | 2005-192880 A | 7/2005 |
| JP | 2009-172287 A | 8/2009 |

\* cited by examiner

ANTENNA CONNECTION UNIT, RECEIVED STRENGTH CORRECTION APPARATUS AND CAPSULE ENDOSCOPE SYSTEM

CROSS REFERENCES TO RELATED APPLICATIONS

This application is a continuation of PCT international application Ser. No. PCT/JP2012/076834 filed on Oct. 17, 2012 which designates the United States, incorporated herein by reference, and which claims the benefit of priority from Japanese Patent Applications No. 2011-232185, filed on Oct. 21, 2011, incorporated herein by reference.

BACKGROUND OF THE INVENTION

1. Field of the Invention

The present invention relates to an antenna connection unit, a received strength correction apparatus, and a capsule endoscope system.

2. Description of the Related Art

An endoscope is widely used as a medical observation instrument that is introduced into a subject to observe inside a body cavity of the subject. In recent years, a swallowable endoscope (capsule endoscope) has been developed, which includes an imaging device and a communication device that wirelessly transmits image data captured by the imaging device, in a capsule-shaped casing.

The capsule endoscope is swallowed from a mouth of the subject to observe inside the body cavity, moves inside organs such as an esophagus, a stomach, and a small intestine following their peristaltic motion until it is naturally excreted from the subject, and sequentially captures images while moving inside the organs. Image data captured by the capsule endoscope inside the body cavity while the capsule endoscope moves inside the body cavity is sequentially transmitted to outside the body by a wireless transmission and accumulated in a memory provided inside or outside an external receiving device or displayed on a display provided on the receiving device.

A doctor or a nurse can load the image data accumulated in the memory to an information processing apparatus via a cradle into which the receiving device is plugged and perform a diagnosis of the subject based on the image displayed on a display of the image processing apparatus or the image displayed on the display of the receiving device.

When receiving a wireless signal from the capsule endoscope, in the receiving device, in general, a plurality of receiving antennas is arranged outside the subject in a distributed manner, one antenna having the strongest received strength is selected, and the wireless signal is received by the selected antenna. For example, a receiving device that switches a reception among a plurality of antennas arranged outside a subject and detects a position of a capsule endoscope inside the subject, which is a transmission source of the wireless signal, based on the electric field strength received by each of the antennas has been known (see, for example, Japanese Laid-open Patent Publication No. 2003-000608). In addition, a technique for detecting a position of a capsule endoscope by estimating the position from reception power of a plurality of receiving antennas has been known.

SUMMARY OF THE INVENTION

An antenna connection unit according to one aspect of the invention is an antenna connection unit to which a plurality of receiving antennas for receiving a wireless signal transmitted from a capsule endoscope which is introduced into a subject to acquire image data inside the subject, is connectable. The antenna connection unit includes: a received electric field strength detector configured to detect received strength of the wireless signal according to a plurality of pieces of input power from the plurality of receiving antennas; a correction parameter generation unit configured to generate a received strength correction parameter for correcting the received electric field strength detector, based on the plurality of pieces of input power and the received strength corresponding to each input power; a correction parameter generation unit configured to generate a received strength correction parameter for correcting the received electric field strength detector, which is obtained by correcting the plurality of pieces of input power and the received strength corresponding to each input power, based on a reference parameter indicating a relationship between each input power and a detection strength obtained by performing a measurement for a received electric field strength detection circuit as a reference in advance; and a storage unit for storing the received strength correction parameter generated by the correction parameter generation unit.

A received strength correction apparatus according to another aspect of the invention is a received strength correction apparatus for correcting a received strength of an antenna connection unit, the antenna connection unit including: a received electric field strength detector configured to detect received strength of a wireless signal according to input power from a plurality of receiving antennas for receiving the wireless signal transmitted from a capsule endoscope which is introduced into a subject to acquire image data inside the subject; and a storage unit configured to store various pieces of information. The received strength correction apparatus includes: a reference power output unit configured to output a plurality of pieces of reference power to the antenna connection unit; a correction parameter generation unit configured to generate a received strength correction parameter for correcting the received electric field strength detector, based on the pieces of reference power output by the reference power output unit and the received strength corresponding to each reference power; and an output unit configured to output the received strength correction parameter generated by the correction parameter generation unit, to the antenna connection unit.

A capsule endoscope system according to another aspect of the invention includes: a capsule endoscope configured to be introduced into a subject to acquire image data inside the subject, convert the image data into a wireless signal, and transmit the wireless signal to outside; a plurality of receiving antennas configured to receive the wireless signal; an antenna connection unit including a received electric field strength detector configured to detect received strength of the wireless signal according to a plurality of pieces of input power from the plurality of receiving antennas; a receiving device to which the antenna connection unit is removably attached; and an image display device configured to acquire the image data via the receiving device and display an image corresponding to the image data. The antenna connection unit includes: a correction parameter generation unit configured to generate a received strength correction parameter for correcting the received electric field strength detector, which is obtained by correcting the plurality of pieces of input power and the received strength corresponding to each input power, based on a reference parameter indicating a relationship between each input power and a detection strength obtained by performing a measurement for a received electric field strength detection circuit as a reference in advance; and a storage unit for storing the received strength correction parameter generated by the correction parameter generation unit.

The above and other features, advantages and technical and industrial significance of this invention will be better understood by reading the following detailed description of presently preferred embodiments of the invention, when considered in connection with the accompanying drawings.

DETAILED DESCRIPTION OF THE PREFERRED EMBODIMENTS

Exemplary embodiments of an antenna connection unit, a receiving device, and a detection strength correction apparatus according to the present invention will be described in detail below with reference to the accompanying drawings. In the following descriptions, a capsule endoscope system including a capsule endoscope that is introduced inside a body of a subject and captures an in-vivo image of the subject is described as an example of the antenna receiving device according to the present invention; however, this embodiment should not be construed to limit the scope of the invention. Further, in the description of each of the drawings, the description is given by assigning the same reference sign to similar elements. Moreover, the drawings are schematic, and hence it should be noted that a dimension and a ratio of each element may differ from actual values. In addition, among the drawings, some elements may have different relationship or ratio of dimensions from each other.

Figure 1:
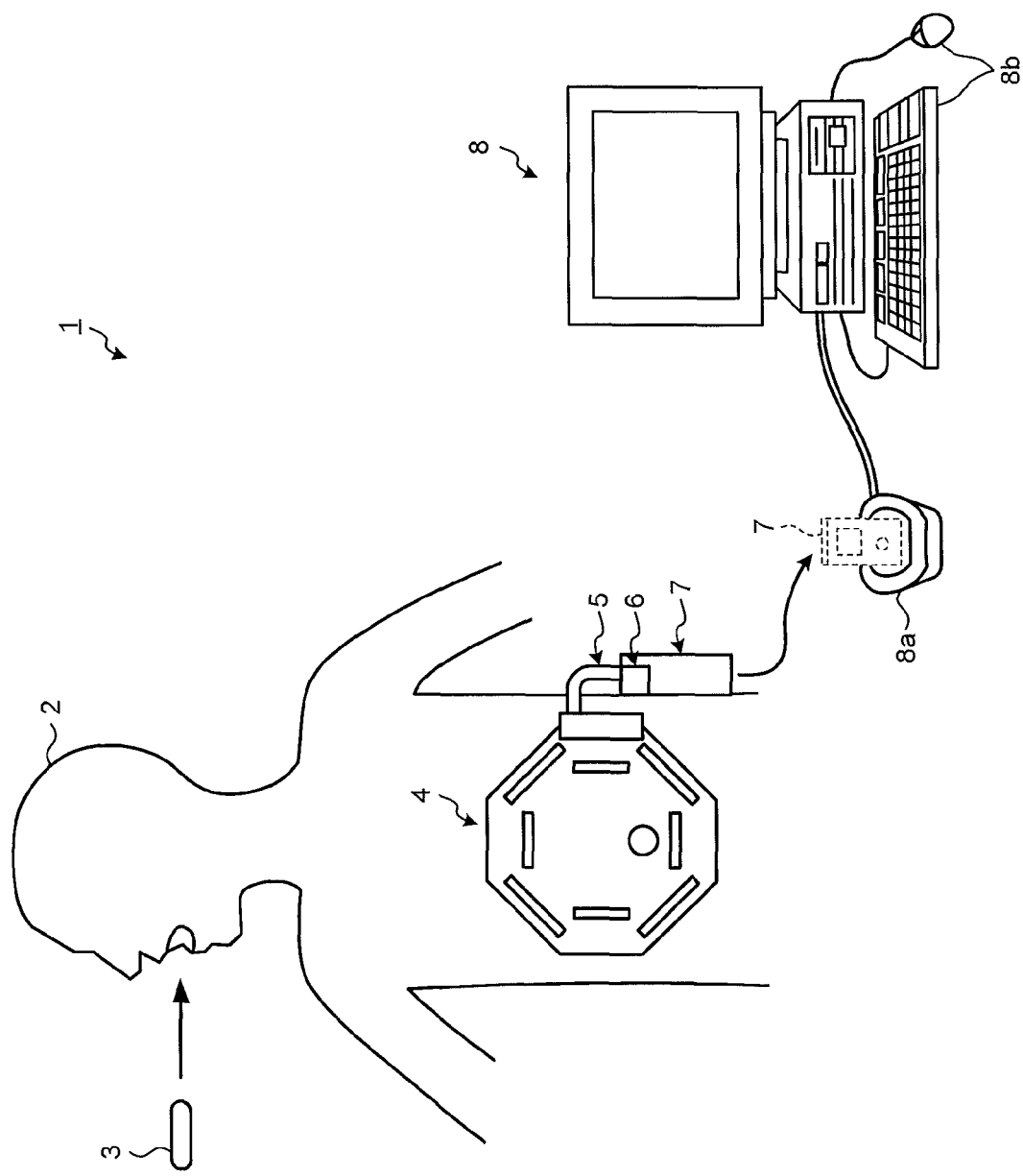
FIG. 1 is a schematic diagram of an overall configuration of a capsule endoscope system according to an embodiment of the present invention.

Firstly, a capsule endoscope system according to the embodiment of the present invention is described in detail with reference to the drawings. FIG. 1 is a schematic diagram of the overall configuration of capsule endoscope system according to the embodiment.

As illustrated in FIG. 1, a capsule endoscope 1 includes a capsule endoscope 3 as a body-insertable apparatus that is introduced into a subject 2 and captures an in-vivo image of the subject 2 by moving inside the subject 2, an acquisition antenna 4 that receives a wireless signal transmitted from the capsule endoscope 3 introduced into the subject 2, an antenna connection unit 6 that performs a specified process on the wireless signal input from the acquisition antenna 4 via an antenna cable 5, a receiving device 7 that performs a specified process on a signal input from the antenna connection unit 6 and stores therein the signal, and an image processing apparatus 8 that performs at least one of a process or a display of an image corresponding to image data inside the subject 2 captured by the capsule endoscope 3. The acquisition antenna 4, the antenna cable 5, and the antenna connection unit 6 and the receiving device 7 constitute a receiving antenna connection unit. The receiving device 7 is inserted in a receiving device holder (not illustrated) and worn on the subject 2. The acquisition antenna 4 is inserted in an antenna holder (not illustrated) and worn on the subject 2.

The capsule endoscope 3 has an imaging function for capturing an image inside the subject 2 and a wireless communication function for transmitting the image data obtained by capturing the image inside the subject 2 to the acquisition antenna 4. Inside the capsule endoscope 3, a circular coil or circular loop antenna is arranged. The capsule endoscope 3 is swallowed by the subject 2, passes an esophagus of the subject 2, and moves inside a body cavity of the subject 2 by a peristaltic motion of a lumen of the gut. The capsule endoscope 3 sequentially captures an image inside the body cavity of the subject 2 at a small time interval, for example, an interval of 0.5 seconds while moving inside the body cavity, generates image data of the image captured inside the subject 2, and sequentially transmits the image data to the acquisition antenna 4. In this case, the capsule endoscope 3 generates a transmission signal including the image data and received strength detection data including position information (beacon) or the like for causing a received strength to be easily detected, and wirelessly transmits a wireless signal obtained by modulating the generated transmission signal to the acquisition antenna 4.

The acquisition antenna 4 periodically receives the wireless signal from the capsule endoscope 3, and outputs the wireless signal to the antenna connection unit 6 via the antenna cable 5. When performing an examination of the subject 2, the acquisition antenna 4 is inserted into an antenna holder and worn on the subject 2 by being fixed with a belt or the like.

The antenna cable 5 is configured by using a coaxial cable. The antenna cable 5 transmits the wireless signal received by the acquisition antenna 4 to the antenna connection unit 6.

The antenna connection unit 6 performs an extraction of the image data of the image inside the subject 2 and a detection of a received strength corresponding to strength of the wireless signal based on the wireless signal wirelessly transmitted from the capsule endoscope 3 via the acquisition antenna 4 and the antenna cable 5.

The receiving device 7 acquires the image data of the image inside the subject 2 based on the wireless signal wirelessly transmitted from the capsule endoscope 3 via the antenna connection unit 6. The receiving device 7 stores the position information, time information indicating time, and the like in a memory in association with the received image data. While the capsule endoscope 3 captures the image, for example, since the capsule endoscope 3 is introduced into the subject 2 from a mouth of the subject 2 until it passes inside the gut and is excreted from the subject 2, the receiving device 7 is accommodated in a receiving device holder and carried by the subject 2. After the examination by the capsule endoscope 3 is over, the receiving device 7 is removed from the subject 2 and connected to the image processing apparatus 8 to transfer information such as the image data received from the capsule endoscope 3 to the image processing apparatus 8.

Further, when the antenna connection unit 6 detects a disconnection of the antenna cable 5, the receiving device 7 performs a display indicating that the antenna is disconnected on a display unit of the receiving device 7 to notify the fact to a user.

Although the display unit of the receiving device 7 has a viewer function to view the acquired image, in order to prevent an excessive use of the viewer function, when a remaining amount of a battery of a power source unit inside the receiving device 7 reaches a level that cannot guarantee an assumed examination time, a notifying unit is provided to notify the fact to the user.

Although it is configured to display the image in real time with the viewer function of the display unit of the receiving device 7, in order to store the image data transmitted from the capsule endoscope 3 in a storage unit (memory) of the receiving device 7 without fail during the real-time display, a data buffer is divided into two systems of a first frame buffer and a second frame buffer, so that a process of stored data is performed in the first frame buffer and a process for the real-time display is performed in the second frame buffer, for example, to make sure that the image data is stored without fail.

In addition, in the receiving device 7, the stored image data can be viewed with a playback view function. When performing a playback view, because the image transmitted from the capsule endoscope 3 is simultaneously received, at the same time as a writing of the image data is performed in the same storage unit, a reading of the image data from the same storage unit 74 is performed. At this time, by using a frame buffer for writing the image data and collectively writing the image data in the memory upon completing a reception of a frame, the writing of the image data in the same storage memory and the reading of the image data from the same storage memory can be performed.

Further, in order to prevent a software hang-up in a state in which an internal software of the receiving device 7 is not completely operating at the time of starting the receiving device 7, a reset function at the time of starting the receiving device 7 and a reset function at the time when an event is generated are provided in a unit other than an internal control unit (CPU) of the receiving device 7. The event is generated when the receiving device 7 is plugged in or removed with respect to a cradle 8a, when a power switch of the receiving device 7 is turned ON/OFF, or the like.

The receiving device 7 is further configured to perform a display of a status of the battery of the power source unit on the image processing apparatus 8 or the receiving device 7 based on information obtained from a circuit that detects a charged capacity and a degradation status installed in the battery inside the receiving device 7.

Moreover, the receiving device 7 is configured to block an access to a button for removing a battery cover in a state in which the antenna connection unit 6 is connected to the receiving device 7 in order to prevent the battery inside the receiving device 7 from being removed during the examination.

In addition, the receiving device 7 includes an LED having a good visibility on an upper portion of the apparatus, so that, when the receiving device 7 is connected to the cradle 8a and an initialization is performed by the image processing apparatus 8 and when the initialization is completed, the completion of the initialization can be notified by the upper-portion LED.

The receiving device 7 further includes a guide that prevents a position of the receiving device 7 from being misaligned when connecting the receiving device 7 to the antenna connection unit 6 and the cradle 8a.

Although the receiving device 7 is used by inserting it into the receiving device holder when wearing on the body, the receiving device holder is configured such that a holder main unit into which the receiving device 7 is inserted and a shoulder belt that is put on a shoulder of the subject 2 are removable from each other in order to make an operator easily view a screen and perform a button operation.

The image processing apparatus 8 is implemented by using a workstation or a personal computer including a display unit such as a liquid crystal display. The image processing apparatus 8 displays an image corresponding to the image data inside the subject 2 acquired via the receiving device 7. The cradle 8a that reads the image data from the memory of the receiving device 7 and operation input devices 8b such as a keyboard and a mouse are connected to the image processing apparatus 8. When the receiving device 7 is mounted on the cradle 8a, the cradle 8a acquires the image data from the memory of the receiving device 7 and acquires related information associated with the image data, such as received strength information, time information, and identification information of the capsule endoscope 3, and transfers the acquired various pieces of information to the image processing apparatus 8. The operation input devices 8b receive an input from the user. With this configuration, the user diagnoses the subject 2 by observing biological parts of the subject 2, such as an esophagus, a stomach, a small intestine, and a large intestine, while monitoring the image inside the subject 2 sequentially displayed by the image processing apparatus 8 with an operation of the operation input devices 8b.

The image processing apparatus 8 is further configured to acquire antenna identification information transmitted from the antenna connection unit 6 via the receiving device 7 and switch a process of the position detection for each antenna type. Further, the image processing apparatus 8 is configured to determine an abnormality based on antenna failure information transmitted from the receiving device 7 and switch a display of the position detection information. The cradle 8a includes a binder for preventing a cable that connects the cradle 8a and the image processing apparatus 8 from being pulled from the cradle 8a.

Figure 2:
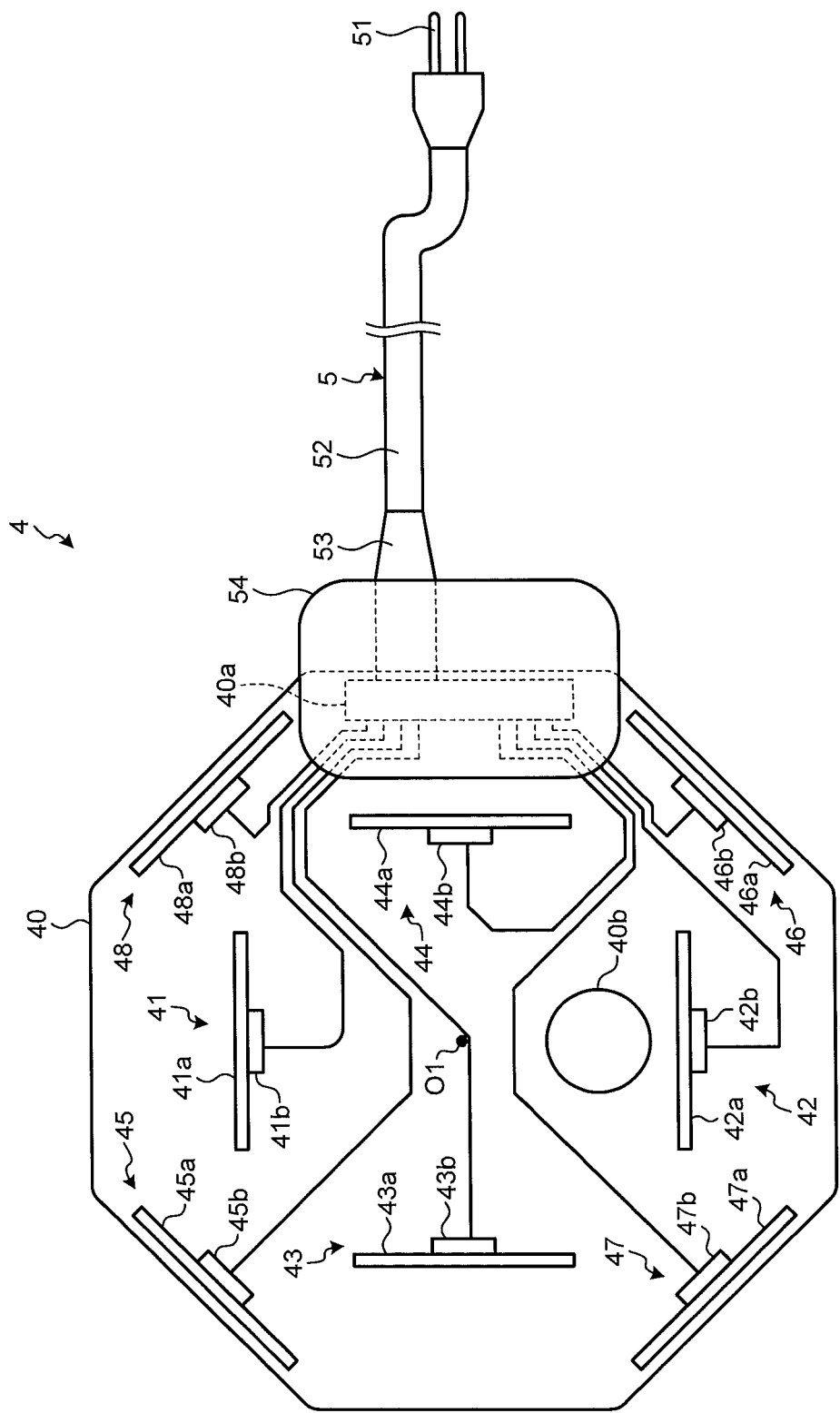
FIG. 2 is a schematic diagram of an acquisition antenna illustrated in FIG. 1.

Detailed configurations of the acquisition antenna 4 and the antenna cable 5 illustrated in FIG. 1 will be described below. FIG. 2 is a schematic diagram of the configurations of the acquisition antenna 4 and the antenna cable 5 illustrated in FIG. 1.

As illustrated in FIG. 2, the acquisition antenna 4 includes a polygon sheet portion 40, a connector unit 40a, a first receiving antenna 41, a second receiving antenna 42, a third receiving antenna 43, a fourth receiving antenna 44, a fifth receiving antenna 45, a sixth receiving antenna 46, a seventh receiving antenna 47, and an eighth receiving antenna 48. The first to eighth receiving antennas 41 to 48 are connected to the connector unit 40a and arranged on a single polygon sheet portion 40. In FIG. 2, a reference point O1 is the center of the polygon sheet portion 40.

The polygon sheet portion 40 is configured by using a sheet-shaped flexible substrate. A main surface of the polygon sheet portion 40 defines substantially an octagon shape. The polygon sheet portion 40 is formed with a size that covers the entire abdomen surface of the subject 2. The polygon sheet portion 40 includes the connector unit 40a to which the antenna cable 5 is connected and a positioning hole portion 40b of a circular shape.

The connector unit 40a is connected to the antenna cable 5 inside a contact member. The connector unit 40a is connected to the first to eighth receiving antennas 41 to 48 with a planar-shaped transmission line (strip line).

The center of the positioning hole portion 40b is located at a position separated from the reference point O1 of the polygon sheet portion 40 of in the downward direction in FIG. 2 by a specified distance. The positioning hole portion 40b functions as a positioning unit for determining a mounting position of the acquisition antenna 4 with respect to the subject 2 when mounting the acquisition antenna 4 on the subject 2. For example, when the polygon sheet portion 40 is attached to the subject 2 such that an index site (for example, a navel) of a front body of the subject 2 is positioned at the center portion of the positioning hole portion 40b, the first to eighth receiving antennas 41 to 48 of the acquisition antenna 4 are accurately mounted on specified mounting positions of the front body of the subject 2. The main surface of the polygon sheet portion 40 is not necessarily be substantially the octagon shape, but can be a rectangular shape, for example.

Further, in order to prevent the polygon sheet portion 40 from being curved at an edge of a cover portion 54 that covers a connection portion of the polygon sheet portion 40 and a proximal end portion 53, the polygon sheet portion 40 has the cover portion 54 formed with an elastic member of which a thickness is decreased from the proximal end portion 53 toward the polygon sheet portion 40. Although the acquisition antenna 4 is inserted into the antenna holder and mounted on the subject 2 during the examination, by forming the acquisition antenna 4 and the antenna holder in an asymmetric shape in the vertical direction or in the horizontal direction, the acquisition antenna 4 is prevented from being inserted into the antenna holder in an upside down state or a reversed side state, thus preventing the acquisition antenna 4 from being mounted on the subject 2 in a wrong direction. Alternatively, a mark for identifying up and down and front and back sides can be displayed on a surface of the acquisition antenna 4.

The first receiving antenna 41 and the second receiving antenna 42 are respectively arranged at positions facing each other across the reference point O1 of the polygon sheet portion 40. The first receiving antenna 41 and the second receiving antenna 42 include an element portion 41a and an element portion 42a, respectively, formed by a printed wiring on the polygon sheet portion 40. The first receiving antenna 41 and the second receiving antenna 42 further include an active circuit 41b and an active circuit 42b, respectively, which are connected to the element portion 41a and the element portion 42a, respectively. The active circuit 41b and the active circuit 42b are formed on the polygon sheet portion 40 by a planar circuit. The active circuit 41b and the active circuit 42b respectively perform impedance matching of the first receiving antenna 41 and the second receiving antenna 42, an amplification process including amplification and attenuation of the received wireless signal, and a conversion process of converting from a balanced state to an unbalanced state. The first receiving antenna 41 and the second receiving antenna 42 are connected to the connector unit 40a formed on the polygon sheet portion 40 by a planar-shaped transmission line (strip line).

The third receiving antenna 43 and the fourth receiving antenna 44 are respectively arranged at positions rotated by 90 degrees on the plane centering around the reference point O1 with respect to the first receiving antenna 41 and the second receiving antenna 42. The third receiving antenna 43 and the fourth receiving antenna 44 include an element portion 43a and an element portion 44a, respectively, formed by a printed wiring on the polygon sheet portion 40. The third receiving antenna 43 and the fourth receiving antenna 44 further include an active circuit 43b and an active circuit 44b, respectively, which are connected to the element portion 43a and the element portion 44a, respectively. The third receiving antenna 43 and the fourth receiving antenna 44 are connected to the connector unit 40a by a planar-shaped transmission line.

The fifth receiving antenna 45 and the sixth receiving antenna 46 are respectively arranged at positions rotated by 45 degrees on the plane centering around the reference point O1 with respect to the first receiving antenna 41 and the second receiving antenna 42. The fifth receiving antenna 45 and the sixth receiving antenna 46 are respectively arranged at the positions on an outer circumferential side on the plane from the first receiving antenna 41 and the second receiving antenna 42. The fifth receiving antenna 45 and the sixth receiving antenna 46 include an element portion 45a and an element portion 46a, respectively, formed by a printed wiring on the polygon sheet portion 40. The fifth receiving antenna 45 and the sixth receiving antenna 46 further include an active circuit 45b and an active circuit 46b, respectively, which are connected to the element portion 45a and the element portion 46a, respectively. The fifth receiving antenna 45 and the sixth receiving antenna 46 are connected to the connector unit 40a by a planar-shaped transmission line.

The seventh receiving antenna 47 and the eighth receiving antenna 48 are respectively arranged at positions rotated by 90 degrees on the plane centering around the reference point O1 with respect to the fifth receiving antenna 45 and the sixth receiving antenna 46. The seventh receiving antenna 47 and the eighth receiving antenna 48 are respectively arranged at the positions on an outer circumferential side on the plane from the first receiving antenna 41 and the second receiving antenna 42. The seventh receiving antenna 47 and the eighth receiving antenna 48 include an element portion 47a and an element portion 48a, respectively, formed by a printed wiring on the polygon sheet portion 40. The seventh receiving antenna 47 and the eighth receiving antenna 48 further include an active circuit 47b and an active circuit 48b, respectively, which are connected to the element portion 47a and the element portion 48a, respectively. The seventh receiving antenna 47 and the eighth receiving antenna 48 are connected to the connector unit 40a by a planar-shaped transmission line.

The acquisition antenna 4 configured in the above manner can arrange relative positions of the receiving antennas with high accuracy with respect to an intralumen where the capsule endoscope 3 passes, which is an internal organ of the subject 2, by arranging the first to eighth receiving antennas 41 to 48 with reference to a portion that becomes an index of the front body of the subject 2. With this arrangement, a positioning of the acquisition antenna 4 on the subject 2 can be easily performed by a simple operation of attaching the acquisition antenna 4 on the subject 2 by using the positioning hole portion 40b. A transparent member, for example, a transparent vinyl sheet can be provided on the positioning hole portion 40b.

The antenna cable 5 transmits the wireless signals respectively received by the first to eighth receiving antennas 41 to 48 to the antenna connection unit 6, and transfers a power supplied from the antenna connection unit 6 to the first to eighth receiving antennas 41 to 48. The antenna cable 5 includes a connection plug portion 51, a cable portion 52, and the proximal end portion 53. The connection plug portion 51 is plugged into a cable connector on a side of the antenna connection unit 6, thus making a connection to the antenna connection unit 6. The cable portion 52 includes as many cores as the number of the first to eighth receiving antennas 41 to 48. Specifically, the cable portion 52 includes eight cores. The proximal end portion 53 is connected at a position separated by a specified distance on a straight line passing the reference point O1 with respect to the connector unit 40a.

Figure 3:
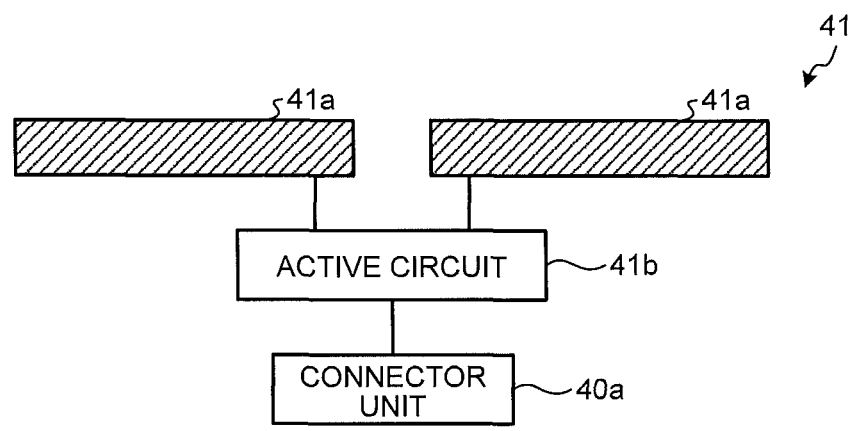
FIG. 3 is a block diagram of a first receiving antenna illustrated in FIG. 2.

A configuration of the first receiving antenna 41 illustrated in FIG. 2 will be described in detail below. FIG. 3 is a block diagram of the first receiving antenna 41 illustrated in FIG. 2.

As illustrated in FIG. 3, the first receiving antenna 41 is configured by using a balanced-type antenna. Specifically, the element portion 41a of the first receiving antenna 41 is configured by using a dipole antenna including two linear electric lead. The first receiving antenna 41 is formed by the two linear electric leads of the element portion 41a having substantially the same length in a laterally symmetric shape. With this configuration, the first receiving antenna 41 has a large loss of a crossing polarized wave with respect to a primary polarized wave. The above-mentioned second to eighth receiving antennas 42 to 48 have the same configuration as the first receiving antenna 41, and hence a description thereof is omitted. Further, although the number of the receiving antennas is eight in the first embodiment, it is not limited to eight.

Figure 4:
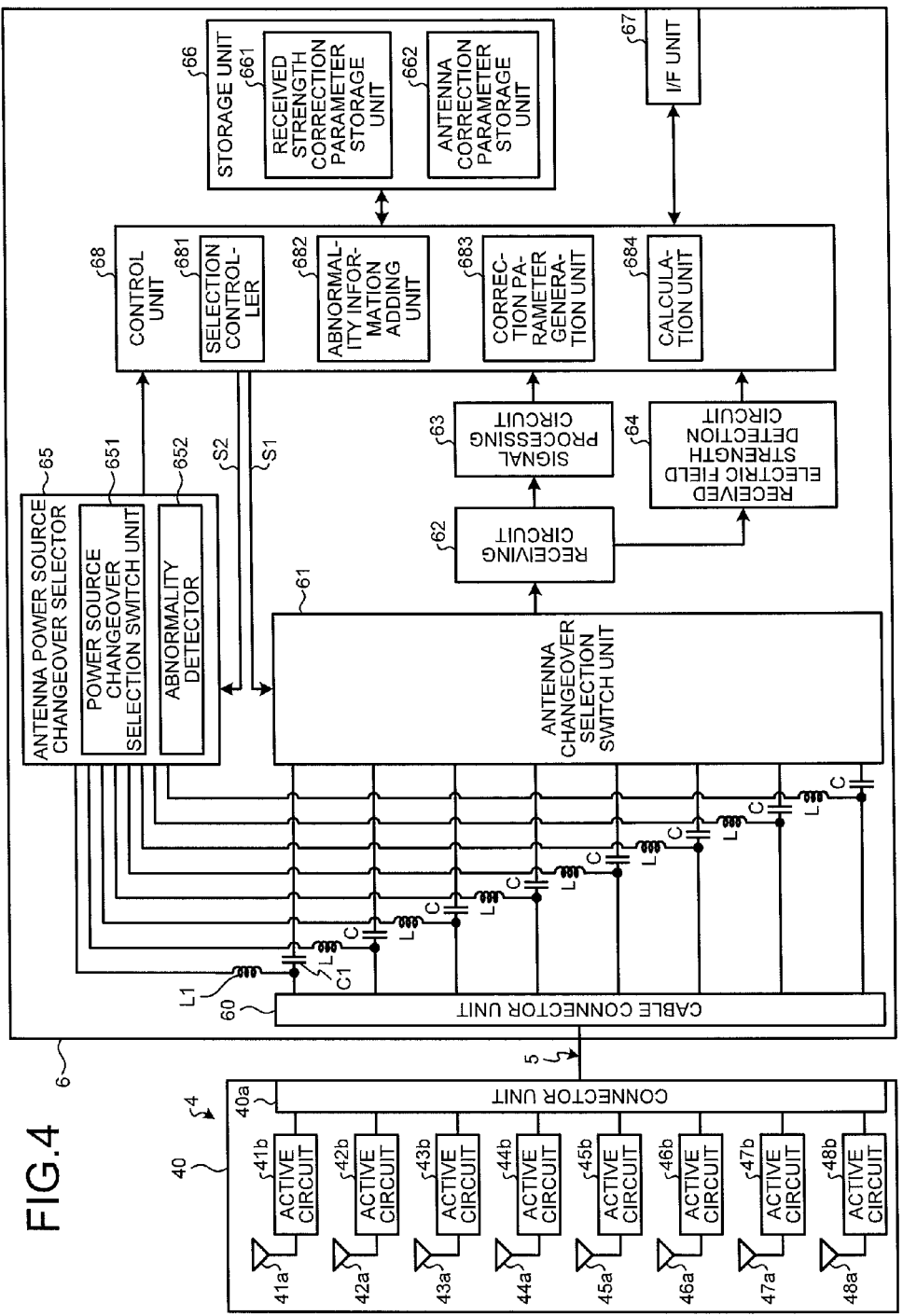
FIG. 4 is a schematic diagram of an antenna connection unit illustrated in FIG. 1.

A configuration of the antenna connection unit 6 illustrated in FIG. 1 will be described below. FIG. 4 is a schematic diagram of the antenna connection unit 6 illustrated in FIG. 1. In the following descriptions, when indicating any one of the first to eighth receiving antennas 41 to 48, the description is given simply referring to the first receiving antenna 41 (element portion 41a and active circuit 41b).

As illustrated in FIG. 4, the antenna connection unit 6 includes a cable connector unit 60 to which the antenna cable 5 is connected, an antenna changeover selection switch unit 61 that selectively switches the first to eighth receiving antennas 41 to 48, a receiving circuit 62 that performs a process such as a demodulation with respect to the wireless signal received via one of the first to eighth receiving antennas 41 to 48 selected by the antenna changeover selection switch unit 61, a signal processing circuit 63 that extracts image data and the like from the wireless signal output from the receiving circuit 62, a received electric field strength detection circuit 64 that detects a received strength based on a strength of the wireless signal output from the receiving circuit 62, an antenna power source changeover selector 65 that supplies a power to one of the first to eighth receiving antennas 41 to 48, a storage unit 66 that stores a correction parameter for correcting the received electric field strength detection circuit 64 and a correction parameter for correcting the first to eighth receiving antennas 41 to 48, an I/F unit 67 that performs bidirectional transmission and reception with the receiving device 7, and a control unit 68 that controls an operation of the antenna connection unit.

The antenna cable 5 is removably connected to the cable connector unit 60. The cable connector unit 60 is electrically connected to the antenna changeover selection switch unit 61 and the antenna power source changeover selector 65.

The antenna changeover selection switch unit 61 is configured by using a mechanical switch, a semiconductor switch, or the like. The antenna changeover selection switch unit 61 is electrically connected to each of the first to eighth receiving antennas 41 to 48 via a capacitor C1. When a changeover signal S1 for switching the receiving antenna that receives the wireless signal is input from the control unit 68, the antenna changeover selection switch unit 61 selects, for example, the first receiving antenna 41 that is designated by the changeover signal S1, and outputs the wireless signal received via the selected first receiving antenna 41 to the receiving circuit 62. Capacitances of the capacitors respectively connected to the first to eighth receiving antennas 41 to 48 are the same as capacitance of the capacitor C1.

The receiving circuit 62 performs a specified process on the wireless signal received via the first receiving antenna 41 that is selected by the antenna changeover selection switch unit 61, such as a process of demodulation or amplification, and outputs the processed signal to the signal processing circuit 63 and the received electric field strength detection circuit 64. The receiving circuit 62 is configured by using a filter, an amplifier, a mixer, and the like.

The signal processing circuit 63 extracts the image data from the wireless signal input from the receiving circuit 62, performs a specified process on the extracted image data, such as various image processing, an A/D conversion process, and the like, and outputs the processed data to the control unit 68. Specifically, the signal processing circuit 63 performs an amplification process, a noise reduction process, and the like, and outputs the processed data to the control unit 68.

The received electric field strength detection circuit 64 detects received strength corresponding to the strength of the wireless signal input from the receiving circuit 62, and adds a gain of the receiving circuit 62 and a gain of the received electric field strength detection circuit 64 itself to generate a received strength signal (RSSI: Received Signal Strength Indicator), and outputs the received strength signal to the control unit 68.

The antenna power source changeover selector 65 is electrically connected to each of the first to eighth receiving antennas 41 to 48 via a coil L1. The antenna power source changeover selector 65 supplies a power, for example, to the first receiving antenna 41 that is selected by the antenna changeover selection switch unit 61 via the antenna cable 5. The antenna power source changeover selector 65 includes a power source changeover selection switch unit 651 and an abnormality detector 652. Electrical characteristics of the coils respectively connected to the first to eighth receiving antennas 41 to 48 are the same as an electrical characteristic of the coil L1.

The power source changeover selection switch unit 651 is configured by using a mechanical switch, a semiconductor switch, or the like. When a selection signal S2 for selecting the receiving antenna to which the power is supplied is input from the control unit 68, the power source changeover selection switch unit 651 selects, for example, the first receiving antenna 41 that is designated by the selection switch S2, and supplies the power to the selected first receiving antenna 41 only.

When an abnormality is generated in the first receiving antenna 41 that supplies the power, the abnormality detector 652 outputs to the control unit 68 an abnormal signal indicating that the abnormality is generated in the first receiving antenna 41 that supplies the power. Specifically, the abnormality detector 652 detects an abnormality of disconnection or an abnormality of short-circuit in the first receiving antenna 41 based on a voltage supplied to the first receiving antenna 41 that is selected by the power source changeover selection switch unit 651, and outputs the detection result to the control unit 68.

The storage unit 66 is configured by using semiconductor memory such as flash memory and random access memory (RAM) provided in a fixed manner inside the antenna connection unit 6. The storage unit 66 stores therein the image data captured by the capsule endoscope 3, various pieces of information associated with the image data, such as position information of the capsule endoscope 3, received strength information, and identification information for identifying a receiving antenna that received the wireless signal, various programs executed by the antenna connection unit 6, and the like. The storage unit 66 includes a received strength correction parameter storage unit 661 that stores therein a received strength correction parameter for correcting the received strength detected by the received electric field strength detection circuit 64 and an antenna correction parameter storage unit 662 that stores therein an antenna correction parameter for correcting the received power of the first to eighth receiving antennas 41 to 48. Each of the received strength correction parameter storage unit 661 and the antenna correction parameter storage unit 662 stores therein a result obtained by performing a correction process that will be described later.

The I/F unit 67 has a function as a communication interface, and performs a bidirectional reception and transmission with the receiving device 7. In this embodiment, the I/F unit 67 functions as an output unit.

The control unit 68 is configured by using a central processing unit (CPU) or the like. The control unit 68 controls the overall operation of the antenna connection unit 6 by loading and executing the program from the storage unit 66 and performing an instruction to each of the components constituting the antenna connection unit 6, a transfer of data, and the like.

A detailed configuration of the control unit 68 will be described below. The control unit 68 includes a selection controller 681, an abnormality information adding unit 682, a correction parameter generation unit 683, and a calculation unit 684.

The selection controller 681 selects a receiving antenna for receiving the wireless signal transmitted from the capsule endoscope 3, and performs control of supplying the power only to the selected receiving antenna. Specifically, the selection controller 681 selects a receiving antenna for receiving the wireless signal transmitted from the capsule endoscope 3 based on the received strength (input power) of each of the first to eighth receiving antennas 41 to 48 detected by the received electric field strength detection circuit 64, and performs control of supplying the power only to the selected receiving antenna. For example, the selection controller 681 drives the antenna changeover selection switch unit 61 for each specified timing, for example, for each interval of 100 msec, and sequentially selects a receiving antenna for receiving the wireless signal from among the first to eighth receiving antennas 41 to 48, and performs this process repeatedly until the received strength detected by the received electric field strength detection circuit 64 reaches a specified value.

When an abnormality is detected in any one of the first to eighth receiving antennas 41 to 48 by the abnormality detector 652, the abnormality information adding unit 682 adds abnormality information indicating that an abnormality is generated in one of the first to eighth receiving antennas 41 to 48 for the wireless signal received by each of the first to eighth receiving antennas 41 to 48. Specifically, the abnormality information adding unit 682 adds a flag indicating the abnormality information to the image data on which the signal processing is performed by the signal processing circuit 63 with respect to the wireless signal received by each of the first to eighth receiving antennas 41 to 48.

The correction parameter generation unit 683 generates a received strength correction parameter for correcting the received electric field strength detection circuit 64 based on a plurality of pieces of input power different from each other input to the received electric field strength detection circuit 64 and the received strength corresponding to each input power. The correction parameter generation unit 683 stores the generated received strength correction parameter in the received strength correction parameter storage unit 661. Further, the correction parameter generation unit 683 generates an antenna correction parameter for correcting the received power of the first to eighth receiving antennas 41 to 48 based on a difference value between a reference power transmitted to each of the first to eighth receiving antennas 41 to 48 and received power received by each of the first to eighth receiving antennas 41 to 48. The correction parameter generation unit 683 stores the generated antenna correction parameter in the antenna correction parameter storage unit 662.

The calculation unit 684 calculates a correction value obtained by correcting the received strength detected by the received electric field strength detection circuit 64 by referring to the received strength correction parameter stored in the received strength correction parameter storage unit 661 and the antenna correction parameter stored in the antenna correction parameter storage unit 662.

Figure 5:
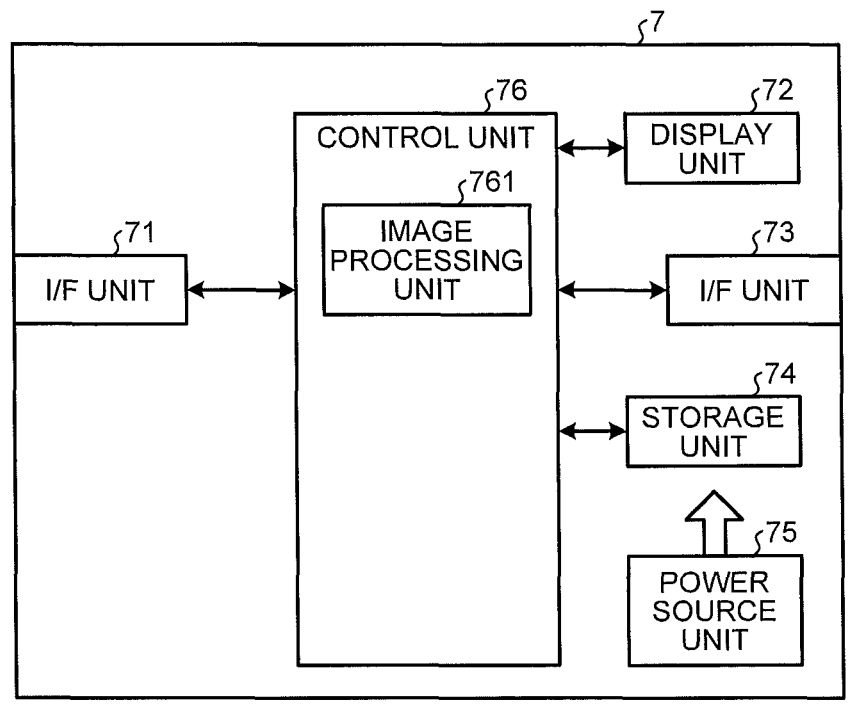
FIG. 5 is a block diagram of a receiving device illustrated in FIG. 1.

The receiving device 7 illustrated in FIG. 1 will be described below. FIG. 5 is a block diagram of the receiving device 7 illustrated in FIG. 1.

As illustrated in FIG. 5, the receiving device 7 includes an I/F unit 71 that performs a bidirectional transmission and reception with the antenna connection unit 6, a display unit 72 that displays an image corresponding to the image data received from the capsule endoscope 3 via the antenna connection unit 6, an I/F unit 73 that performs a bidirectional communication with the image processing apparatus 8 via the cradle 8a, a storage unit 74 that stores various pieces of information including the image data received from the capsule endoscope 3 via the acquisition antenna 4, the antenna cable 5, and the antenna connection unit 6, a power source unit 75 that supplies a power to each of the components of the acquisition antenna 4, the antenna connection unit 6, and the receiving device 7, and a control unit 76 that controls an operation of the receiving device 7.

The I/F unit 71 has a function as a communication interface, and performs a bidirectional communication with the antenna connection unit 6.

The display unit 72 is configured by using a display panel including a liquid crystal display panel, an organic electro luminescence (EL) display panel, or the like. The display unit 72 displays the image corresponding to the image data captured by the capsule endoscope 3 and various pieces of information including an operation status of the antenna connection unit 6, an operation status of the receiving device 7, patient information of the subject 2, examination date and time, and the like.

The I/F unit 73 has a function as a communication interface, and performs a bidirectional communication with the image processing apparatus 8 via the cradle 8a.

The storage unit 74 is configured by using semiconductor memory such as flash memory and RAM provided in a fixed manner inside the receiving device 7. The storage unit 74 stores therein the image data captured by the capsule endoscope 3 and various pieces of information associated with the image data, such as position information of the capsule endoscope 3, received strength information, and identification information for identifying a receiving antenna that received the wireless signal. The storage unit 74 further stores therein various programs executed by the receiving device 7. Alternatively, the information can be externally stored in a recording medium such as a memory card, and the storage unit 74 can have a function as a recording medium interface for loading the information stored in the recording medium.

The power source unit 75 is configured by using a battery removably mounted on the receiving device 7 and a switch unit that switches on and off states of the battery. The power source unit 75 supplies required driving power to each of the constituent elements of the receiving device 7, the antenna connection unit 6, and the acquisition antenna 4 in the on state, and stops supplying the driving power to each of the constituent elements of the receiving device 7, the antenna connection unit 6, and the acquisition antenna 4.

The control unit 76 is configured by using a CPU or the like. The control unit 76 controls the overall operation of the receiving device 7 by loading and executing the program from the storage unit 74 and performing an instruction to each of the components constituting the receiving device 7, a transfer of data, and the like. The control unit 76 includes an image processing unit 761.

The image processing unit 761 performs a specified image processing on the image data output from the antenna connection unit 6 via the I/F unit 71, and stores the processed image data in the storage unit 74. Specifically, the image processing unit 761 performs image processing including at least a gain process for adjusting a brightness of the image, a gradation correction process for correcting a gradation, an edge process, a white balance process, a color correction process, and a γ correction process on the image data. Further, the image processing unit 761 may compress the image data based on the JPEG system, and stores the compressed image data in the storage unit 74.

Figure 6:
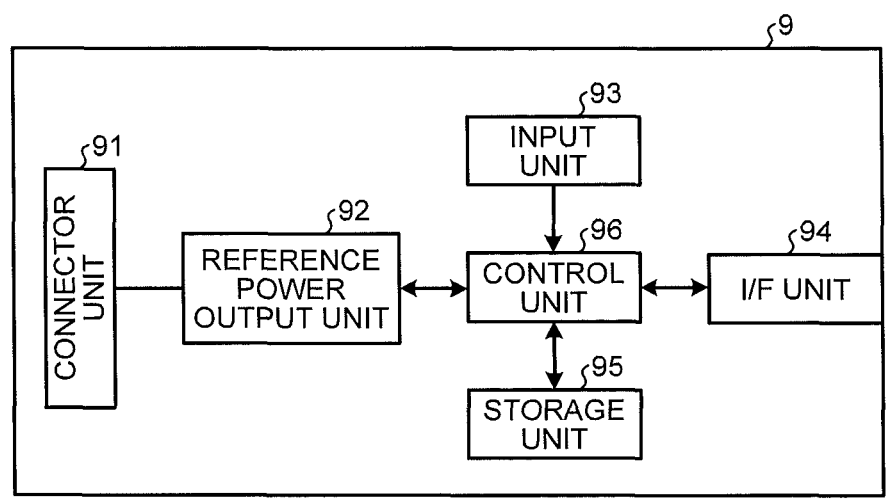
FIG. 6 is a block diagram of a received strength correction apparatus.

In the receiving antenna connection unit configured in the above manner, because the received strength detected by the received electric field strength detection circuit 64 of the antenna connection unit 6 fluctuates from one individual to the next, a received strength correction apparatus (hereinafter, an "RSSI correction apparatus") used when correcting the fluctuation is described below. FIG. 6 is a block diagram of an RSSI correction apparatus 9.

As illustrated in FIG. 6, the RSSI correction apparatus 9 includes a connector unit 91 that is electrically connected to the antenna connection unit 6 via the antenna cable 5, a reference power output unit 92 that outputs a reference power to the received electric field strength detection circuit 64 of the antenna connection unit 6, an input unit 93 that receives an input of a command signal for instructing a level of input power input to the antenna connection unit 6, an I/F unit 94 that performs a bidirectional transmission and reception with the antenna connection unit 6, a storage unit 95 that stores a program executed by the RSSI correction apparatus 9 and a control unit 96 that controls an operation of the RSSI correction apparatus 9.

The connector unit 91 is connected to the reference power output unit 92. By connecting the antenna cable 5 to the connector unit 91, the reference power of the reference power output unit 92 is output to the antenna connection unit 6.

The reference power output unit 92 outputs input power (reference power) of different levels to the antenna connection unit 6 under control of the control unit 96. Specifically, the reference power output unit 92 outputs a plurality of reference power different from each other, for example, reference power of −100 dBm to −10 dBm at specified intervals to the antenna connection unit 6 via the antenna cable 5 and the connector unit 91.

The input unit 93 receives command information for instructing a start of the RSSI correction apparatus 9, command information for instructing a level of the input power input to the antenna connection unit 6, and various pieces of other command information, and inputs the received information to the control unit 96. The input unit 93 is configured by using a touch panel, a mechanical switch, or the like.

The I/F unit 94 has a function as a communication interface, and performs a bidirectional transmission and reception with the antenna connection unit 6.

The storage unit 95 is configured by using semiconductor memory such as flash memory and RAM provided in a fixed manner inside the RSSI correction apparatus 9. The storage unit 95 further stores therein various programs executed by the RSSI correction apparatus 9. The storage unit 95 may further stores therein the received strength output from the antenna connection unit 6 via the I/F unit 94 and the control unit 96.

The control unit 96 causes the reference power output unit 92 to output the input power to the antenna connection unit 6 based on a command signal input from the input unit 93. Specifically, the control unit 96 causes the reference power output unit 92 to output a plurality of reference power different from each other to the antenna connection unit 6 based on the command signal input from the input unit 93. The control unit 96 further causes the reference power output unit 92 to output the reference power as the input power to the antenna connection unit 6 under control of the correction parameter generation unit 683 of the antenna connection unit 6.

Figure 7:
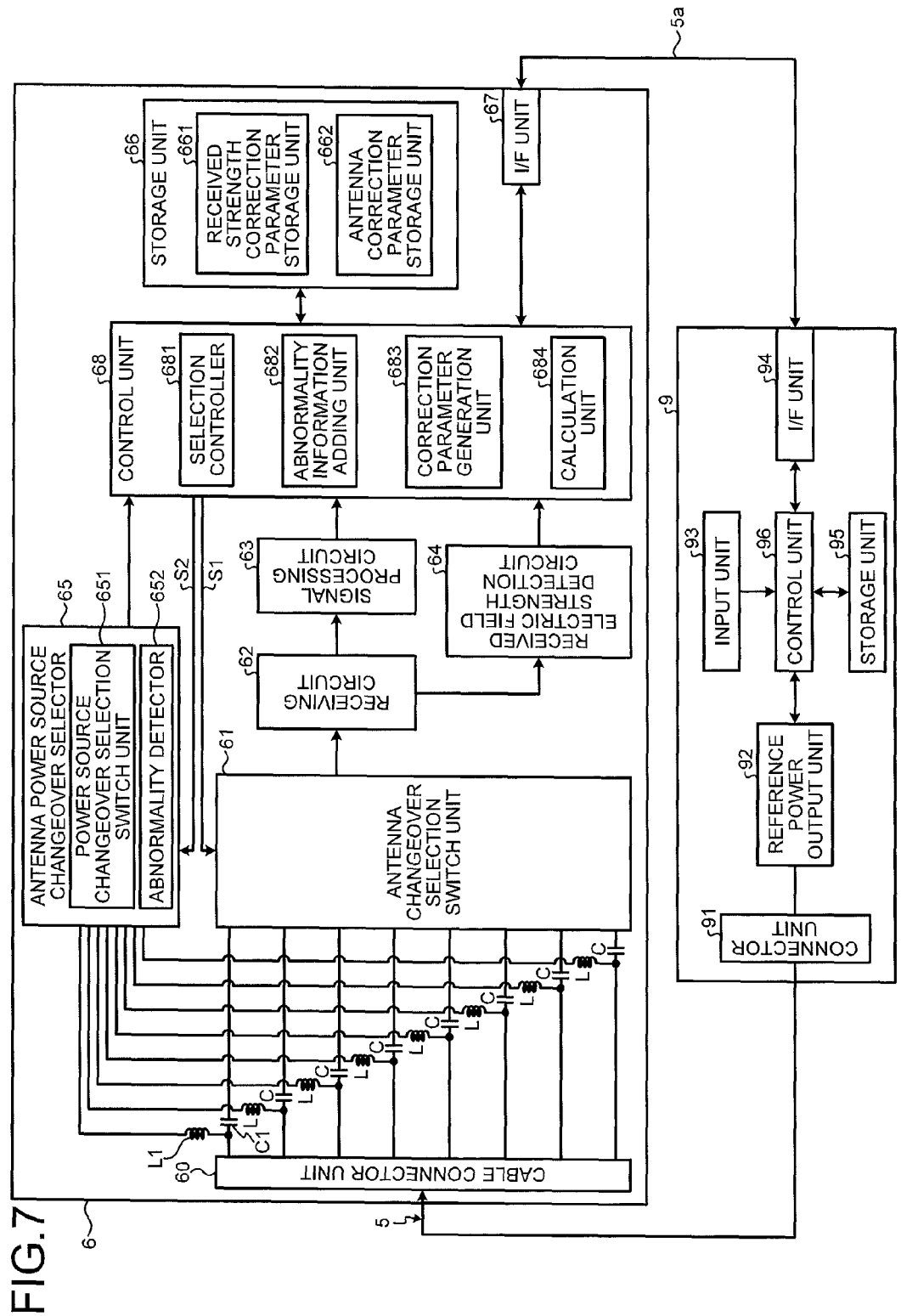
FIG. 7 is a schematic diagram of a configuration when a correction parameter generation unit generates a received strength correction parameter by using a received electric field strength detection circuit of the antenna connection unit and the received strength correction apparatus.
Figure 8:
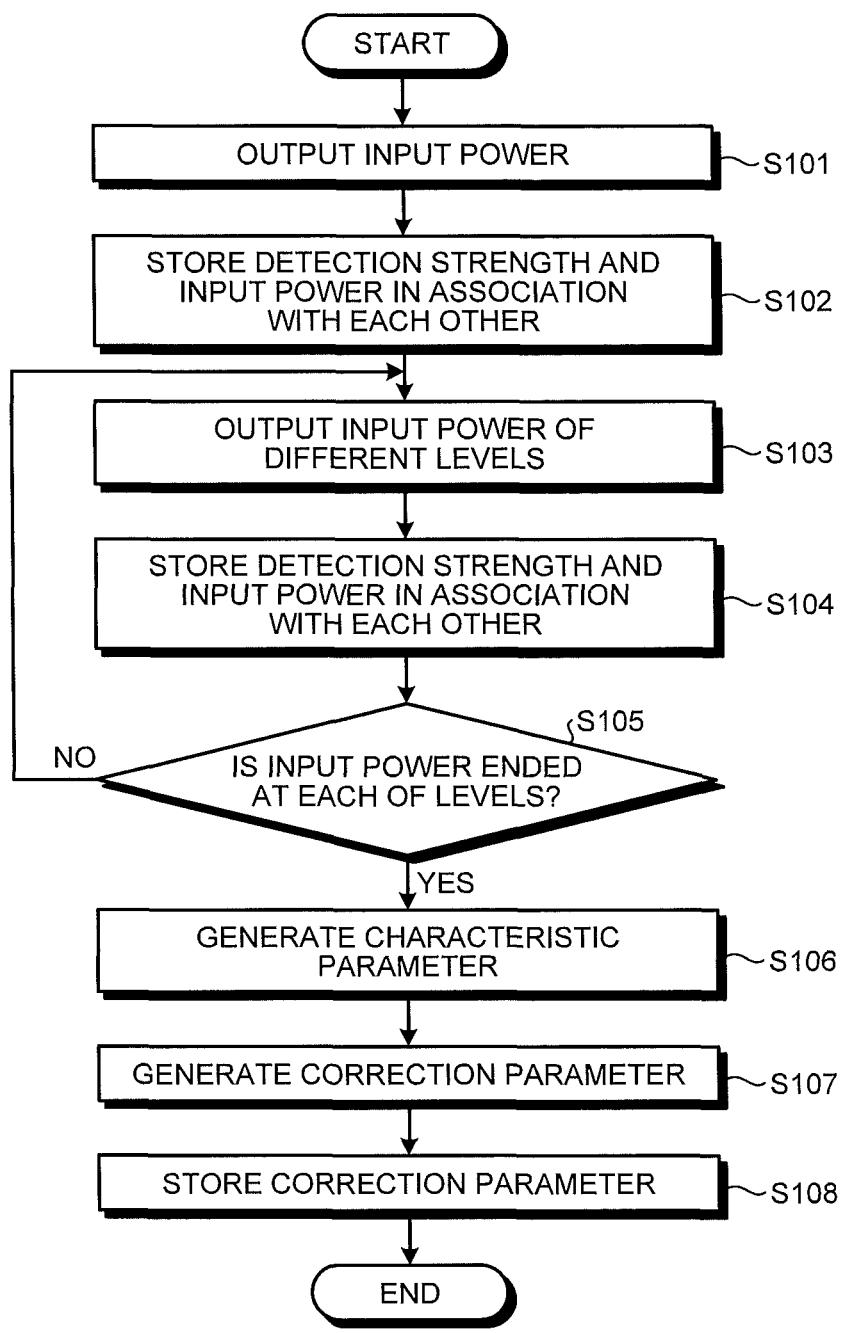
FIG. 8 is a flowchart of a process when the antenna connection unit according to the embodiment of the present invention generates the received strength correction parameter.

Reference will be made to a method of generating a correction parameter used when correcting the detection strength of the received electric field strength detection circuit 64 of the antenna connection unit 6 by using the RSSI correction apparatus 9 configured in the above manner. FIG. 7 is a schematic diagram of a configuration when the correction parameter generation unit 683 generates the received strength correction parameter by using the received electric field strength detection circuit 64 of the antenna connection unit 6 and the RSSI correction apparatus 9. FIG. 8 is a flowchart of a process when the antenna connection unit 6 generates the received strength correction parameter. The reference power output unit 92 of the RSSI correction apparatus 9 and the cable connector unit 60 of the antenna connection unit 6 are electrically connected to each other via the antenna cable 5. The I/F unit 94 of the RSSI correction apparatus 9 and the I/F unit 67 of the antenna connection unit 6 are electrically connected to each other via a communication cable 5a.

As illustrated in FIG. 8, the correction parameter generation unit 683 causes the reference power output unit 92 to output the input power (reference power) via the I/F unit 67, the I/F unit 94, and the control unit 96 (Step S101), and stores the input power output by the reference power output unit 92 in the storage unit 66 in association with the detection strength detected by the received electric field strength detection circuit 64 (Step S102).

Subsequently, the correction parameter generation unit 683 causes the reference power output unit 92 to output input power of a difference power level via the I/F unit 67, the I/F unit 94, and the control unit 96 (Step S103), and stores the input power output by the reference power output unit 92 in the storage unit 66 in association with the detection strength detected by the received electric field strength detection circuit 64 (Step S104).

Thereafter, the correction parameter generation unit 683 determines whether or not each input power (a plurality of points) by the reference power output unit 92 is ended (Step S105). When it is determined that each input power by the reference power output unit 92 is ended (YES at Step S105), the correction parameter generation unit 683 moves to Step S106. On the other hand, when it is determined that each input power by the reference power output unit 92 is not ended (NO at Step S105), the correction parameter generation unit 683 returns to Step S103.

At Step S106, the correction parameter generation unit 683 generates a characteristic parameter of the received electric field strength detection circuit 64 based on a correspondence relationship of the detection strength stored in the storage unit 66 and each input power. Specifically, the correction parameter generation unit 683 generates the characteristic parameter of the received electric field strength detection circuit 64, which indicates a relationship between each input power and the detection strength, by performing a linear correction (linear interpolation) or a nonlinear correction (nonlinear interpolation) by using each of the detection strength of the received electric field strength detection circuit 64 stored in the storage unit 66 and each input power associated with each of the detection strength.

Thereafter, the correction parameter generation unit 683 generates the received strength correction parameter obtained by correcting the characteristic parameter by referring to a reference parameter of the received electric field strength detection circuit 64 stored in the storage unit 66 (Step S107). The reference parameter mentioned here is a characteristic parameter for the received electric field strength detection circuit 64, which serves as a reference for a calibration.

Figure 9:
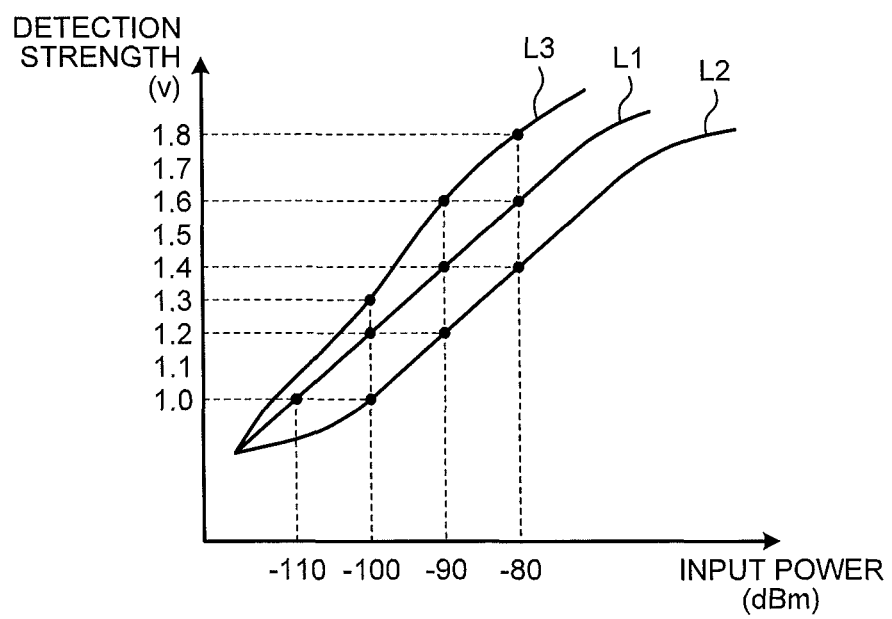
FIG. 9 is a graph illustrating a relationship between a detection strength detected by the received electric field strength detection circuit and input power.

FIG. 9 is a graph illustrating a relationship between a detection strength detected by the received electric field strength detection circuit 64 and input power. In FIG. 9, the horizontal axis represents the input power (dBm) by the reference power output unit 92, and the vertical axis represents the detection strength (v) by the received electric field strength detection circuit 64. In FIG. 9, a curved line L1 indicates the reference parameter of the detection strength corresponding to each input power, a curved line L2 indicates an example of the characteristic parameter of the detection strength corresponding to each input power before the correction, and a curved line L3 indicates an example of another characteristic parameter of the detection strength corresponding to each input power before the correction.

Figure 10:
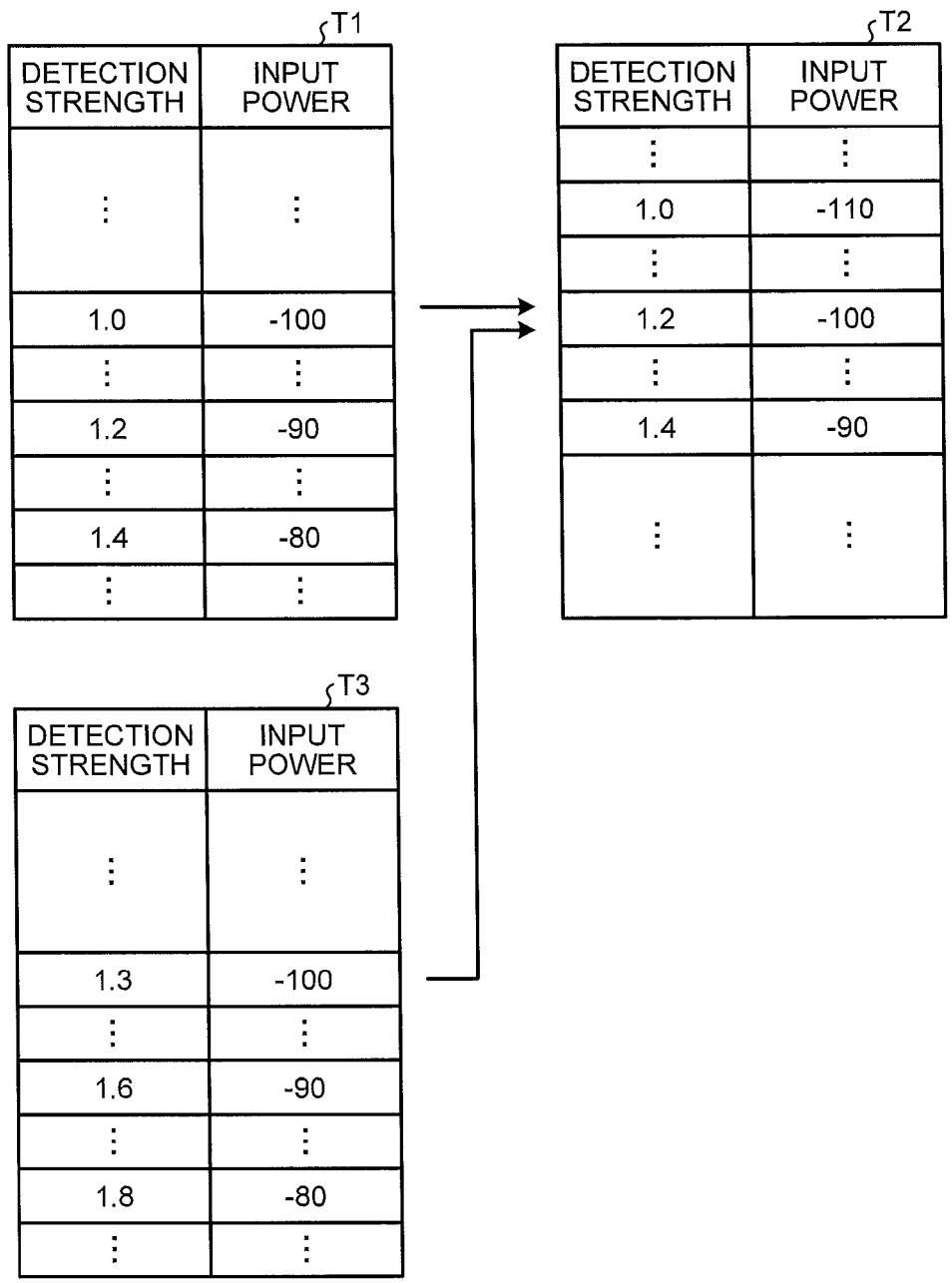
FIG. 10 is an explanatory diagram for illustrating a method of generating the received strength correction parameter by the correction parameter generation unit.

As illustrated in FIG. 9, the correction parameter generation unit 683 corrects the characteristic parameter of the detection strength (the curved line L2 or the curved line L3) by referring to the reference parameter (the curved line L1). Specifically, as illustrated in FIG. 10, the correction parameter generation unit 683 generates a received strength correction parameter table T2 by correcting a characteristic parameter table T1 that indicates a correspondence relationship of the detection strength of the received electric field strength detection circuit 64 stored in the storage unit 66 and each input power by referring to the reference parameter (the curved line L1) of the detection strength. Further, the correction parameter generation unit 683 generates the received strength correction parameter table T2 by correcting a characteristic parameter table T3 that indicates a correspondence relationship of the detection strength of the received electric field strength detection circuit 64 stored in the storage unit 66 and each input power by referring to the reference parameter (the curved line L1) of the detection strength. For example, as illustrated in FIG. 10, in the case of the characteristic parameter table T1, the correction parameter generation unit 683 generates the received strength correction parameter table T2 by performing a correction such that the detection strength becomes 1.2 (v) for the input power of −100 (dBm) when the detection strength of 1.0 (v) is stored for the input power of −100 (dBm). Further, as illustrated in FIG. 10, in the case of the characteristic parameter table T3, the correction parameter generation unit 683 generates the received strength correction parameter table T2 by performing a correction such that the detection strength becomes 1.2 (v) for the input power of −100 (dBm) when the detection strength of 1.3 (v) is stored for the input power of −100 (dBm).

In this manner, the correction parameter generation unit 683 generates the received strength correction parameter by correcting the detection strength corresponding to each input power generated by the linear correction or the nonlinear correction by referring to the reference parameter stored in the storage unit 66. Alternatively, the correction parameter generation unit 683 can generate the received strength correction parameter table T2 by calculating a slope from each of the detection strength and performing a correction such that the slope matches the reference parameter.

Referring back to FIG. 8, a process after Step S108 is described below. At Step S108, the correction parameter generation unit 683 stores the received strength correction parameter in the received strength correction parameter storage unit 661, and ends the process.

Figure 11:
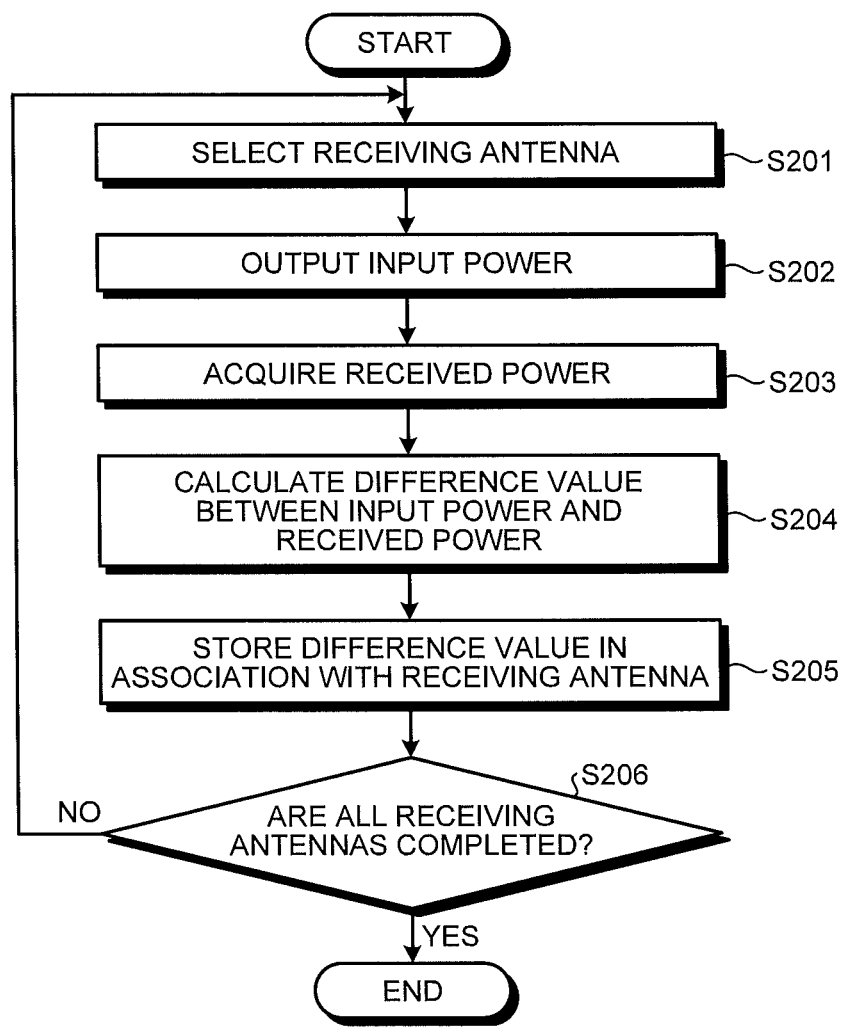
FIG. 11 is a flowchart of a process when the antenna connection unit according to the embodiment of the present invention generates an antenna correction parameter.

Next, reference will be made to a method of generating an antenna correction parameter that is used when correcting the received power the acquisition antenna 4 receives by using the RSSI correction apparatus 9. FIG. 11 is a flowchart of a process when the antenna connection unit 6 generates the antenna correction parameter. The acquisition antenna 4 is connected to the antenna connection unit 6 via the antenna cable 5. Further, a sheet-shaped jig having a plurality of transmission antennas respectively facing the arrangement positions of the first to eighth receiving antennas 41 to 48 is connected to the connector unit 91 of the RSSI correction apparatus 9 via the antenna cable 5.

As illustrated in FIG. 11, the correction parameter generation unit 683 selects a receiving antenna for receiving the input power (Step S201). Specifically, the correction parameter generation unit 683 selects the first receiving antenna 41 as the receiving antenna for receiving the input power by driving the antenna changeover selection switch unit 61.

Subsequently, the correction parameter generation unit 683 causes the reference power output unit 92 to output the input power via the I/F unit 67, the I/F unit 94, and the control unit 96 (Step S202), and acquires the received power the first receiving antenna 41 receives via the received electric field strength detection circuit 64 (Step S203).

Subsequently, the correction parameter generation unit 683 calculates a difference value between the input power output by the reference power output unit 92 and the received power of the first receiving antenna 41 acquired via the received electric field strength detection circuit 64 (Step S204).

Thereafter, the correction parameter generation unit 683 stores the calculated difference value in association with the receiving antenna that received the input power in the antenna correction parameter storage unit 662 (Step S205).

Subsequently, the correction parameter generation unit 683 determines whether or not the calculation of the difference value is completed for the received power of all antennas of the acquisition antenna 4 (Step S206). When it is determined that the calculation of the difference value is not completed for the received power of all the receiving antennas (NO at Step S206), the correction parameter generation unit 683 returns to Step S201. On the other hand, when it is determined that the calculation of the difference value is completed for the received power of all the receiving antennas (YES at Step S206), the correction parameter generation unit 683 ends the process.

According to the embodiment of the present invention described above, the correction parameter generation unit 683 generates the received strength correction parameter for correcting the received electric field strength detection circuit 64 based on the correspondence relationship between the input power of different levels and the received strengths of the received electric field strength detection circuit 64 respectively corresponding to the input power of different levels, and stores the received strength correction parameter in the received strength correction parameter storage unit 661. With this configuration, the fluctuation of the gain generated between individuals of the received electric field strength detection circuit 64 can be prevented, and hence a position estimation of the capsule endoscope 3 can be performed with higher accuracy.

Further, according to the embodiment of the present invention, the correction parameter generation unit 683 generates the antenna correction parameter for correcting the first to eighth receiving antennas 41 to 48 based on the difference value between a specified power transmitted to each of the first to eighth receiving antennas 41 to 48 and the received power each of the first to eighth receiving antennas 41 to 48 receives, and stores the antenna correction parameter in the antenna correction parameter storage unit 662. With this configuration, the fluctuation of the gain generated between individuals of the first to eighth receiving antennas 41 to 48 can be prevented, and hence, a position estimation of the capsule endoscope 3 can be performed with higher accuracy.

Moreover, according to the embodiment of the present invention, the calculation unit 684 calculates the correction value obtained by correcting the received strength detected by the received electric field strength detection circuit 64 by performing a correction of the antenna correction parameter stored in the antenna correction parameter storage unit 662 after performing a correction of the received strength correction parameter stored in the received strength correction parameter storage unit 661. With this configuration, the fluctuation of the gain generated between individuals of the first to eighth receiving antennas 41 to 48 can be prevented, and hence, a position estimation of the capsule endoscope 3 can be performed with higher accuracy.

Further, according to the embodiment of the present invention, the first to eighth receiving antennas 41 to 48 includes the active circuits 41b to 48b, respectively, and hence the wireless signal transmitted from the capsule endoscope 3 can be received without bringing the first to eighth receiving antennas 41 to 48 into tight contact with the subject 2.

Moreover, according to the embodiment of the present invention, so long as an emission pattern of the wireless signal transmitted by the capsule endoscope 3 and a shape of the transmission antenna of the capsule endoscope 3, which transmits the wireless signal in a direction of the polarized wave, are known, the position of the capsule endoscope 3 in the subject 2 can be easily estimated by measuring the received strength for all the first to eighth receiving antennas 41 to 48 and searching the position and the direction of the capsule endoscope 3 while matching received strength balances of the first to eighth receiving antennas 41 to 48.

Further, according to the embodiment of the present invention, the capsule endoscope 3 modulates the image data captured in the subject 2, and transmits the modulated image data as the wireless signal. Therefore, the image data can be restored without fail by receiving and demodulating the wireless signal with a receiving antenna having the strongest received strength among the first to eighth receiving antennas 41 to 48.

Moreover, according to the embodiment of the present invention, the correction of the received strength correction parameter stored in the received strength correction parameter storage unit 661 can also be performed after performing the correction of the antenna correction parameter stored in the antenna correction parameter storage unit 662.

Modification Example 1

In the above-mentioned embodiment, the calculation unit 684 calculates the correction value obtained by correcting the received strength detected by the received electric field strength detection circuit 64 by referring to the received strength correction parameter stored in the received strength correction parameter storage unit 661 and the antenna correction parameter stored in the antenna correction parameter storage unit 662; however, the receiving device 7 or the image processing apparatus 8 can also calculate the correction value. In this case, the antenna connection unit 6 outputs the received strength correction parameter stored in the received strength correction parameter storage unit 661, the antenna correction parameter storage unit 662, and the received strength detected by the received electric field strength detection circuit 64 to the receiving device 7 or the image processing apparatus 8 via the I/F unit 67, and the control unit of the receiving device 7 or the image processing apparatus 8 calculates the correction value obtained by correcting the received strength. With this configuration, the processing performance of the control unit 68 of the antenna connection unit 6 can be moderated, and at the same time, the calculation speed of the correction value can be increased.

Modification Example 2

In the above-mentioned embodiment, the antenna connection unit 6 includes the correction parameter generation unit 683, the calculation unit 684, and the received strength correction parameter storage unit 661; however, the receiving device 7 can include the correction parameter generation unit 683, the calculation unit 684, and the received strength correction parameter storage unit 661. With this configuration, the processing performance of the control unit 68 of the antenna connection unit 6 can be moderated, and at the same time, the calculation speed of the correction value can be increased. In this case, the received strength correction parameter and the antenna correction parameter generated by the correction parameter generation unit 683 can be stored in the storage unit 66 of the antenna connection unit 6.

Modification Example 3

In the above-mentioned embodiment, the antenna connection unit 6 includes the correction parameter generation unit 683; however, the RSSI correction apparatus 9 can include the correction parameter generation unit 683. With this configuration, the processing performance of the control unit 68 of the antenna connection unit 6 can be moderated, and at the same time, the program capacity can be reduced, and hence the circuit can be downsized. In this case, the received strength correction parameter and the antenna correction parameter generated by the correction parameter generation unit 683 can be stored in the storage unit 66 of the antenna connection unit 6. Further, the calculation unit 684 of the antenna connection unit 6 can refer to the correction value obtained by correcting the received strength detected by the received electric field strength detection circuit 64 by referring to the received strength correction parameter and the antenna correction parameter generated by the RSSI correction apparatus 9 and respectively stored in the received strength correction parameter storage unit 661 and the antenna correction parameter storage unit 662 of the storage unit 66.

Modification Example 4

In the above-mentioned embodiment, the antenna connection unit 6 includes the correction parameter generation unit 683, the calculation unit 684, and the received strength correction parameter storage unit 661; however, the image processing apparatus 8 can include the correction parameter generation unit 683, the calculation unit 684, and the received strength correction parameter storage unit 661. With this configuration, the processing performance of the control unit 68 of the antenna connection unit 6 can be moderated, and at the same time, the calculation speed of the correction value can be increased. In this case, the received strength correction parameter and the antenna correction parameter generated by the correction parameter generation unit 683 can be stored in the storage unit 66 of the antenna connection unit 6.

Further, in the above-mentioned embodiment, the abnormality detector 652 detects the abnormality of the first to eighth receiving antennas 41 to 48 based on the voltage; however, the abnormality of the first to eighth receiving antennas 41 to 48 can be detected based on at least one of the current or the voltage. In addition, the abnormality detector 652 can detect the abnormality of the first to eighth receiving antennas 41 to 48 based on a combination of the voltage, the current, and the power.

Moreover, in the above-mentioned embodiment, the antenna connection unit 6 and the receiving device 7 can be provided in an integrated manner. In addition, the acquisition antenna 4, the antenna connection unit 6, and the receiving device 7 can be provided in an integrated manner.

Further, in the above-mentioned embodiment, the first to eighth receiving antennas 41 to 48 are formed on the polygon sheet portion 40 in an integrated manner; however, the first to eighth receiving antennas 41 to 48 can also be formed separately.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An antenna connection unit to which a plurality of receiving antennas for receiving a wireless signal transmitted from a capsule endoscope which is introduced into a subject to acquire image data inside the subject, is connectable, the antenna connection unit comprising:
    a received electric field strength detector configured to detect received strength of the wireless signal according to a plurality of pieces of input power from the plurality of receiving antennas;
    a correction parameter generation unit configured to cause the received electric field strength detector to input pieces of reference power as the pieces of input power, and to generate a received strength correction parameter for correcting the received strength which is obtained by the received electric field strength detector with respect to the pieces of input power from the plurality of receiving antennas, based on the pieces of reference power and the received strength detected by the received electric field strength detector according to the pieces of input power; and
    a storage unit for storing the received strength correction parameter generated by the correction parameter generation unit.

2. The antenna connection unit according to claim 1, wherein
    the correction parameter generation unit is configured to generate an antenna correction parameter for correcting the plurality of receiving antennas based on a difference value between specified power transmitted to each of the plurality of receiving antennas and received power received by each of the plurality of receiving antennas, and
    the storage unit stores the antenna correction parameter.

3. The antenna connection unit according to claim 2, further comprising a calculation unit configured to calculate a correction value obtained by correcting the received strength detected by the received electric field strength detector by referring to the received strength correction parameter and the antenna correction parameter stored in the storage unit.

4. The antenna connection unit according to claim 2, further comprising an output unit configured to output the received strength correction parameter, the antenna correction parameter, and the received strength detected by the received electric field strength detector to outside.

5. The antenna connection unit according to claim 1, wherein each of the receiving antennas is a dipole antenna to which an active circuit is connected.

6. A received strength correction apparatus for correcting a received strength of an antenna connection unit, the antenna connection unit including: a received electric field strength detector configured to detect received strength of a wireless signal according to input power from a plurality of receiving antennas for receiving the wireless signal transmitted from a capsule endoscope which is introduced into a subject to acquire image data inside the subject; and a storage unit configured to store various pieces of information, the received strength correction apparatus comprising:
    a reference power output unit configured to output a plurality of pieces of reference power to the antenna connection unit;
    a correction parameter generation unit configured to generate a received strength correction parameter for correcting the received electric field strength detector, based on the pieces of reference power output by the reference power output unit and the received strength corresponding to each reference power; and
    an output unit configured to output the received strength correction parameter generated by the correction parameter generation unit, to the antenna connection unit.

7. The received strength correction apparatus according to claim 6, wherein
    the correction parameter generation unit is configured to generate an antenna correction parameter for correcting each of the plurality of receiving antennas, based on a difference value between specified power transmitted to each of the plurality of receiving antennas and received power received by each of the plurality of receiving antennas, and
    the storage unit stores the antenna correction parameter.

8. The received strength correction apparatus according to claim 6, wherein each of the receiving antennas is a dipole antenna to which an active circuit is connected.

9. A capsule endoscope system, comprising:
a capsule endoscope configured to be introduced into a subject to acquire image data inside the subject, convert the image data into a wireless signal, and transmit the wireless signal to outside;
a plurality of receiving antennas configured to receive the wireless signal;
an antenna connection unit including a received electric field strength detector configured to detect received strength of the wireless signal according to a plurality of pieces of input power from the plurality of receiving antennas;
a receiving device to which the antenna connection unit is removably attached; and
an image display device configured to acquire the image data via the receiving device and display an image corresponding to the image data, wherein
the antenna connection unit comprises:
a correction parameter generation unit configured to cause the received electric field strength detector to input pieces of reference power as the pieces of input power, and to generate a received strength correction parameter for correcting the received strength which is obtained by the received electric field strength detector with respect to the pieces of input power from the plurality of receiving antennas, based on the pieces of reference power and the received strength detected by the received electric field strength detector according to the pieces of input power; and
a storage unit for storing the received strength correction parameter generated by the correction parameter generation unit.

10. The capsule endoscope system according to claim 9, wherein
the correction parameter generation unit is configured to generate an antenna correction parameter for correcting the plurality of receiving antennas, based on a difference value between specified power transmitted to each of the plurality of receiving antennas and received power received by each of the plurality of receiving antennas, and
the storage unit stores the antenna correction parameter.

11. The capsule endoscope system according to claim 9, wherein the each of the receiving antennas is a dipole antenna to which an active circuit is connected.

* * * * *